United States Patent [19]

Ono et al.

[11] 4,366,157
[45] Dec. 28, 1982

[54] NOVEL POLYCYCLIC INDOLE DERIVATIVES

[75] Inventors: Keiichi Ono, Osaka; Hajime Kawakami, Takarazuka; Junki Katsube, Toyonaka, all of Japan

[73] Assignee: Sumitomo Chemical Company, Limited, Osaka, Japan

[21] Appl. No.: 287,039

[22] Filed: Jul. 27, 1981

[30] Foreign Application Priority Data

Aug. 6, 1980 [JP] Japan ................................ 55-108495

[51] Int. Cl.³ ................................................ C07D 46/00
[52] U.S. Cl. .................................... 424/256; 542/404; 546/51
[58] Field of Search ................ 424/262, 256; 542/404; 546/51

[56] References Cited

U.S. PATENT DOCUMENTS

| | | | |
|---|---|---|---|
| 3,318,877 | 5/1967 | Ulshafer et al. | 542/404 |
| 3,331,855 | 7/1967 | Popelak et al. | 542/404 |
| 3,492,304 | 1/1970 | Shavel et al. | 424/262 |
| 3,702,325 | 11/1972 | Fellion | 542/404 |
| 3,957,981 | 5/1976 | Amselem | 424/262 |
| 3,974,164 | 8/1976 | Navarron | 542/404 |
| 4,045,443 | 8/1977 | Pfäffli | 424/262 |
| 4,316,028 | 2/1982 | Katsube et al. | 546/51 |

FOREIGN PATENT DOCUMENTS 2323423 12/1973 Fed. Rep. of Germany .

*Primary Examiner*—Arthur P. Demers
*Attorney, Agent, or Firm*—Stevens, Davis, Miller & Mosher

[57] ABSTRACT

A compound of the formula,

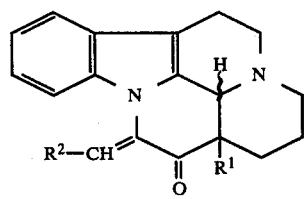

wherein $R^1$ is $C_1$–$C_6$ alkyl group and $R^2$ is aryl group, which is a medicine useful to treat cerebral arteriosclerosis, senile mental indolence and cerebral insufficiency.

10 Claims, No Drawings

NOVEL POLYCYCLIC INDOLE DERIVATIVES

This invention relates to novel eburnane derivatives, and a process for production thereof.

The novel eburnane derivatives provided by the present invention are those represented by the formula [I]:

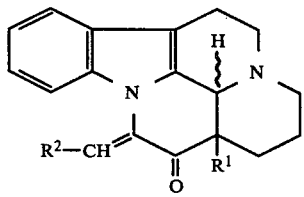

wherein $R^1$ is a $C_1$-$C_6$ alkyl group and $R^2$ is an aryl group.

Among the eburnane derivatives of the formula [I], the preferred compounds are those in which $R^1$ is an ethyl group.

In the significances as used above, the term "$C_1$-$C_6$ alkyl" means a straight or branched chain alkyl group having from 1 to 6 carbon atoms (e.g., methyl, ethyl, n-propyl, iso-propyl, n-butyl, n-pentyl, isobutyl, n-hexyl, etc.) and the term "aryl group" means phenyl, pyridyl, thienyl, furyl, biphenylyl, naphthyl optionally substituted with 1 to 3 substituents selected from the group consisting of halogen, $C_1$-$C_4$ alkyl, $C_1$-$C_4$ alkoxy, trifluoromethyl, hydroxyl, amino and nitro.

Animal tests have revealed that the eburnane derivatives [I] have various pharmacological activities, particularly, a cerebral vasodilating activity and an antihypoxic activity.

Therefore they are a medicine useful to treat cerebral arteriosclerosis, senile mental indolence and cerebral insufficiency.

According to the present invention, the eburnane derivative [I] can be prepared by reacting the ketone derivative of the formula:

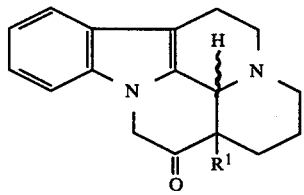

wherein $R^1$ is as defined above with the aldehyde compound of the formula:

$R^2$—CHO wherein $R^2$ is as defined above.

The reaction of the compound [II] with the compound [III] is usually carried out in the presence of a base in an inert solvent such as an aromatic hydrocarbon (e.g. benzene, toluene, xylene), an amide (e.g. dimethylformamide), an ether (e.g. dioxane, tetrahydrofuran), an alcohol (e.g. ethanol, propanol) or an aqueous alcohol at a temperature within a range of room temperature to the boiling point of the solvent employed.

Examples of the suitable base are metal hydride (e.g. sodium hydride, calcium hydride), alkali carbonate (e.g. sodium carbonate, potassium carbonate), alkali hydroxide (e.g. sodium hydroxide, potassium hydroxide), alkali alkoxide (e.g. sodium ethoxide, sodium methoxide) and triethylamine.

The ketone compound [II] used as an intermediate in the present invention can be prepared by the several known procedures, for example, the procedure disclosed in European Patent Publication No. 0 013 315.

The thus prepared eburnane compound [I] can be readily converted into its inorganic or organic acid addition salts by a conventional procedure.

For the preparation of pharmaceutical compositions, they may be mixed with carriers, diluents, lubricants, fillers and/or binders such as lactose, sucrose, calcium phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like. They can be administered in an oral, rectal or other non-oral manner or by a local manner. The usual oral dosage of the active ingredient is between about 5 mg and about 100 mg daily.

Specific examples of the eburnane compound [I] are as follows.

trans 16-(4-chlorophenyl)methylene-17-oxoeburnane

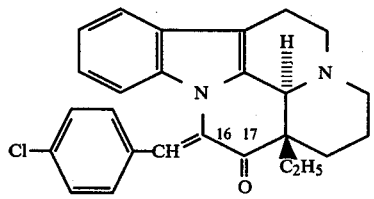

trans 16-(4-hydroxyphenyl)methylene-17-oxoeburnane
trans 16-(4-methylphenyl)methylene-17-oxoeburnane
trans 16-(4-methoxyphenyl)methylene-17-oxoeburnane
trans 16-(4-nitrophenyl)methylene-17-oxoeburnane
trans 16-(4-aminophenyl)methylene-17-oxoeburnane
trans 16-(4-pyridyl)methylene-17-oxoeburnane
trans 16-(2-pyridyl)methylene-17-oxoeburnane
trans 16-(thiophene-3-yl)methylene-17-oxoeburnane
trans 16-(thiophene-2-yl)methylene-17-oxoeburnane
trans 16-(4-phenyl-benzylidene)-17-oxoeburnane
trans 16-(1-naphthyl)methylene-17-oxoeburnane
trans 16-(2-naphthyl)methylene-17-oxoeburnane
trans 16-(furan-2-yl)methylene-17-oxoeburnane
trans 16-benzylidene-17-oxoeburnane
and these cis isomers.

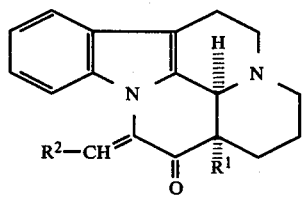

[cis]

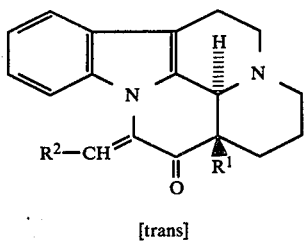

[trans]

Practical and preferred embodiments of the present invention are illustratively shown in the following examples, which are not intended to limit the scope of the invention thereto.

EXAMPLE 1

0.112 g of sodium hydroxide (65%) was added in portion into a solution of 0.34 g of trans 17-oxoeburnane and 0.17 g of benzaldehyde in 10 ml of toluene at room temperature. After stirring for 15 min at 100°–110° C., the resulting mixture was poured into water and extracted with ethyl acetate. The extract was washed with water, dried over anhydrous sodium sulfate and concentrated in vacuo. The residue was crystallized from isopropyl ether to give trans 16-benzylidene-17-oxoeburnane,

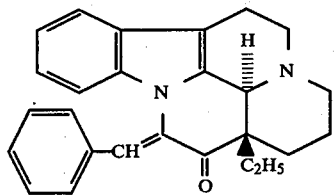

M.P. 139.5°–145.5° C., IR $\nu_{cm^{-1}}{}^{nujol}$ 1690.

EXAMPLE 2

A solution of 2 g of trans-17-oxoeburnane, 0.8 g of 2-thiophenealdehyde and 0.4 g of sodium hydroxide in 8 ml of ethanol was heated under refluxing for 15 min. After cooling, the reaction mixture was diluted with water, and then the precipitated crystals were collected by filtration. The crude crystal was washed with n-hexane to give trans 16-(thiophene-2-yl)methylene-17-oxoeburnane, M.P. 170°–175° C., IR $\nu_{cm^{-1}}{}^{nujol}$ 1695.

EXAMPLE 3

In the same manner as in Example 2, the following compounds were obtained,
trans 16-(furan-2-yl)methylene-17-oxoeburnane M.P. 198°–199.5° C., IR $\nu_{cm^{-1}}{}^{nujol}$ 1685
trans 16-(2-pyridyl)methylene-17-oxoeburnane M.P. 165°–168° C., IR $\nu_{cm^{-1}}{}^{nujol}$ 1710
cis 16-benzylidene-17-oxoeburnane reddish solid, IR $\nu_{cm^{-1}}{}^{nujol}$ 1680–1695 cm$^{-1}$.

What we claim is:
1. A compound of the formula:

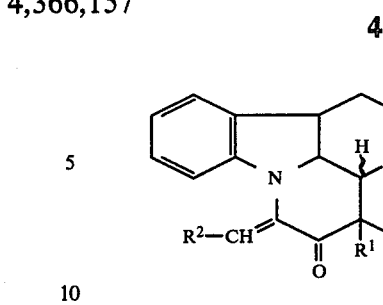

wherein $R^1$ is a $C_1$–$C_6$ alkyl group and $R^2$ is phenyl, pyridyl, thienyl, furyl, biphenylyl or naphthyl optionally substituted with 1 to 3 substituents selected from the group consisting of halogen, $C_1$–$C_4$ alkyl, $C_1$–$C_4$ alkoxy, trifluoromethyl, hydroxyl, amino and nitro.

2. A compound as claimed in claim 1 wherein $R^1$ is an ethyl group.

3. trans 16-benzylidene-17-oxoeburnane and its steroisomer.

4. trans 16-(thiophene-2-yl)methylene-17-oxoeburnane and its stereoisomer.

5. trans 16-(furan-2-yl)methylene-17-oxoeburnane and its stereoisomer.

6. trans 16-(pyridine-2-yl)methylene-17-oxoeburnane and its stereoisomer.

7. A process for producing a compound of the formula:

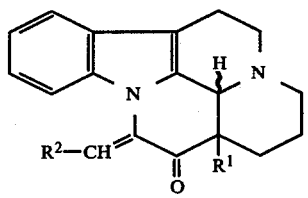

wherein $R^1$ and $R^2$ are each as defined in claim 1, and their non-toxic pharmaceutically acceptable salts, which comprises reacting a compound of the formula:

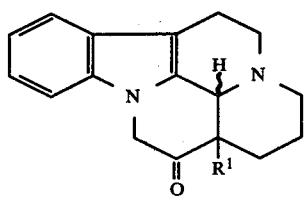

wherein $R^1$ is as defined above with a compound of the formula:

$R^2$—CHO wherein $R^2$ is as defined above.

8. A process according to claim 7, wherein $R^1$ is an ethyl group.

9. A pharmaceutically acceptable acid addition salt of a compound as claimed in claim 1.

10. A pharmaceutical composition for the treatment of cerebral artereosclerosis, senile mental indolence, or cerebral insufficiency comprising a cerebral vasodilating or anti-hypoxic effective amount of a compound as defined in claim 1 and a pharmaceutically acceptable diluent or carrier.

* * * * *